(12) United States Patent
Wayman et al.

(10) Patent No.: US 8,790,302 B2
(45) Date of Patent: *Jul. 29, 2014

(54) PASSIVE REUSE PREVENTION SYRINGE THAT USES A FLANGE LOCK

(75) Inventors: Brian H. Wayman, Morris Plains, NJ (US); Robert Odell, Franklin Lakes, NJ (US); Richard James Caizza, Verona, NJ (US); Andrzej Baranski, Chatham, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 34 days.

This patent is subject to a terminal disclaimer.

(21) Appl. No.: 13/191,910

(22) Filed: Jul. 27, 2011

(65) Prior Publication Data

US 2011/0282279 A1 Nov. 17, 2011

Related U.S. Application Data

(63) Continuation of application No. 12/492,567, filed on Jun. 26, 2009, now Pat. No. 8,066,668.

(51) Int. Cl.
*A61M 5/00* (2006.01)
*A61M 5/315* (2006.01)

(52) U.S. Cl.
USPC .......................................... 604/110; 604/218

(58) Field of Classification Search
USPC .................. 604/110, 111, 218–222
See application file for complete search history.

(56) References Cited

U.S. PATENT DOCUMENTS

| | | | |
|---|---|---|---|
| 4,747,830 A | 5/1988 | Gloyer et al. | |
| 4,850,968 A | 7/1989 | Romano | |
| 4,986,812 A | 1/1991 | Perler | |
| 4,995,870 A * | 2/1991 | Baskas | 604/110 |
| 5,037,393 A | 8/1991 | Ellgass | |

(Continued)

FOREIGN PATENT DOCUMENTS

| | | |
|---|---|---|
| EP | 1106194 | 6/2001 |
| JP | 64-043268 | 2/1989 |

(Continued)

OTHER PUBLICATIONS

Photos of Kojak Selinge (Star Syringe K1) Auto-Disable Syringe with Disposable Needle.

(Continued)

*Primary Examiner* — Nicholas Lucchesi
*Assistant Examiner* — Leah Stohr
(74) *Attorney, Agent, or Firm* — The Webb Law Firm (57) ABSTRACT

A syringe assembly includes a syringe barrel having an inside surface defining a chamber, an open proximal end, a distal end, and an outlet; a plunger assembly disposed at least partially within the syringe barrel, including an elongate plunger rod having a locking flange formed thereon; and a plunger head having a distal sealing surface, the plunger rod being engageable with the plunger head such that the plunger rod is adapted to move the plunger head within the chamber of the syringe barrel through an injection cycle; and a flange lock disposed at the open proximal end of the barrel. The flange lock is integral with the open proximal end of the syringe barrel. During the injection cycle, the flange lock engages the locking flange of the plunger rod so as to prevent removal of the plunger rod from the syringe barrel.

17 Claims, 9 Drawing Sheets

(56) References Cited

U.S. PATENT DOCUMENTS

| | | |
|---|---|---|
| 5,047,017 A | 9/1991 | Koska |
| 5,125,899 A | 6/1992 | Frignoli |
| 5,188,599 A * | 2/1993 | Botich et al. ............... 604/110 |
| 5,211,630 A | 5/1993 | Schmahmann |
| 5,527,284 A | 6/1996 | Ohnemus et al. |
| 5,531,693 A | 7/1996 | Vounatsos |
| 5,533,970 A | 7/1996 | Berger et al. |
| 5,562,623 A | 10/1996 | Shonfeld et al. |
| 5,814,017 A | 9/1998 | Kashmer |
| 5,935,104 A | 8/1999 | Janek et al. |
| 6,117,112 A | 9/2000 | Mahurkar |
| 6,267,749 B1 | 7/2001 | Miklos |
| 6,368,306 B1 | 4/2002 | Koska |
| 6,790,197 B2 | 9/2004 | Kosinski et al. |
| 6,966,898 B1 | 11/2005 | Pouget et al. |
| 7,282,042 B2 | 10/2007 | Wang |
| 7,331,934 B2 | 2/2008 | Suresh et al. |
| 7,393,340 B2 | 7/2008 | Maggioni |
| 7,951,108 B2 | 5/2011 | Harper et al. |
| 8,066,668 B2 * | 11/2011 | Wayman et al. ............... 604/110 |
| 2004/0147875 A1 | 7/2004 | Wallace et al. |
| 2005/0038394 A1 | 2/2005 | Schwarzbich |
| 2005/0159705 A1 | 7/2005 | Crawford et al. |
| 2006/0064060 A1 | 3/2006 | Lin |
| 2007/0106226 A1 | 5/2007 | Croll et al. |
| 2007/0191785 A1 | 8/2007 | Barere et al. |
| 2007/0299395 A1 | 12/2007 | Pelkey et al. |
| 2008/0221529 A1 * | 9/2008 | Kiehne ............... 604/211 |
| 2008/0300550 A1 | 12/2008 | Schiller et al. |
| 2009/0048560 A1 | 2/2009 | Caizza et al. |
| 2009/0076450 A1 | 3/2009 | Caizza et al. |
| 2009/0131869 A1 | 5/2009 | Caizza et al. |

FOREIGN PATENT DOCUMENTS

| | | |
|---|---|---|
| JP | 02-001288 | 1/1990 |
| JP | 02-502073 A | 7/1990 |
| JP | 2003-517857 A | 6/2003 |
| JP | 2007-500543 A | 1/2007 |
| WO | 8810127 | 12/1988 |
| WO | 9803210 | 1/1998 |
| WO | 03/051436 A2 | 6/2003 |
| WO | 2005/039669 A2 | 5/2005 |
| WO | 2005079893 | 9/2005 |
| WO | 2006097105 | 9/2006 |
| WO | 2006/108243 A2 | 10/2006 |
| WO | 2008/106712 A1 | 9/2008 |
| WO | 2008154616 | 12/2008 |
| WO | 2008154630 | 12/2008 |

OTHER PUBLICATIONS

Photos of Neomedic Neoject Auto-Disable Syringe.
Photos of KangKang Autodestruct Syringe.
Photos of Dr. Safe Auto-Destruct Syringe Set.
Kojak Selinge "HMD Injection Procedure" Instruction Sheet, pp. 1-2.
Pictures of 0.5ml safety syringe cady, http://www.emunio.dk/solution/cady/pictures.asp.

* cited by examiner

PASSIVE REUSE PREVENTION SYRINGE THAT USES A FLANGE LOCK

CROSS-REFERENCE TO RELATED APPLICATIONS

This application is a continuation of U.S. application Ser. No. 12/492,567, filed on Jun. 26, 2009, which is hereby incorporated by reference in its entirety.

BACKGROUND OF THE INVENTION

1. Field of the Invention

The present invention relates to a passive reuse prevention syringe that uses a flange lock. More specifically, aspects of the present invention relate to a syringe that includes a flange lock disposed at an open proximal end of a syringe barrel for engaging a locking flange disposed on a plunger rod. The flange lock engages the locking flange so as to prevent removal of the plunger rod from the syringe barrel and disable the syringe.

2. Description of Related Art

Hypodermic syringe products are generally intended for a single use only, in part, to address concerns related to the spread of disease associated with reuse of such products and to deter other misuse. Attempts have been made to provide a solution to these concerns. Some of these attempts have provided injection systems that require a specific, affirmative act to destroy the syringe after the intended injection either by using a separate device for destroying the syringe or providing a syringe assembly with frangible zones so that the syringe could be rendered inoperable by the application of force. Although many of these devices work quite well, they do require the specific intent of the user followed by the affirmative act to destroy or render the syringe inoperable. These devices are not effective with a user having the specific intent to reuse the hypodermic syringe.

Attempts have also been made to provide a syringe assembly that is automatically disabled or rendered inoperable after a single or select number of uses. Such syringe assemblies present specific challenges because they must not prevent filling or use under normal conditions. Moreover, certain automatic locking and disabling devices only allow for a fixed dosage amount to be supplied by the syringe before the syringe is disabled.

SUMMARY OF THE INVENTION

Accordingly, there is a general need for a single use syringe that includes a locking and disabling mechanism that does not operate automatically but that is passively activated through normal use of the syringe. Consequently, a user who has the specific intent to reuse the syringe will actuate the mechanism through normal use of the syringe without consciously realizing that the syringe has been disabled. Such a mechanism will limit the ability of users to reuse the syringe while avoiding the unnecessary costs and dosage limitations of automatic devices.

The present invention overcomes many of the deficiencies present in the prior art by providing a syringe that offers the utility of a traditional syringe along with reuse prevention features and requiring a low force required to activate the reuse prevention mechanism. According to an embodiment of the present invention, the syringe includes a passive reuse prevention mechanism that is activated by the user through normal use of the syringe though the user may not be aware or realize that the mechanism has been activated. The syringe allows for variable dosing, which is important for some procedures, but can also be adapted to deliver fixed doses if required and can be used for injections and/or reconstitution of dry drugs. The syringe is scaleable from the smallest syringe sizes to the largest syringe sizes and allows for reductions of cost compared to current reuse prevention syringes. The syringe is provided with a one or two piece plunger assembly having a sealing surface on a plunger head and a plunger rod, which is engaged by the flange lock on the syringe barrel. Upon or just prior to final injection of the contents of the syringe, the syringe is rendered disabled due to the engagement between flange lock and a locking flange on the plunger rod.

According to an embodiment of the present invention, a syringe assembly is provided. The syringe assembly includes a syringe barrel having an inside surface defining a chamber, an open proximal end, a distal end, and an outlet disposed adjacent the distal end in fluid communication with the chamber; a plunger assembly disposed at least partially within the syringe barrel, including an elongate plunger rod having a proximal end, a distal end, and a locking flange formed thereon between the proximal and distal ends; a plunger head having a distal sealing surface, the plunger rod being engageable with the plunger head such that the plunger rod is capable of moving the plunger head within the chamber of the syringe barrel through an injection cycle; and a flange lock disposed at the open proximal end of the barrel. During the injection cycle, the flange lock engages the locking flange of the plunger rod so as to prevent removal of the plunger rod from the syringe barrel.

The flange lock includes a plurality of flexible protrusions distributed around a periphery of the open proximal end of the syringe barrel. The protrusions are integral with the open proximal end of the syringe barrel and may extend proximally from the open proximal end of the syringe barrel or distally from the open proximal end of the syringe barrel into the chamber of the barrel. The syringe barrel further includes an outwardly extending flange at the open proximal end thereof.

The plunger rod has a cylindrical shape defining an outer surface and the flexible protrusions of the flange lock are adapted to flex toward the inside surface of the barrel as the plunger rod is inserted into the chamber of the barrel. During the injection cycle, the protrusions slide along the outer surface of the plunger rod and engage the locking flange on the plunger rod so as to retain the plunger assembly in a bottomed out position and disable the syringe assembly.

The locking flange on the plunger rod tapers outwardly from the outer surface of the plunger rod so as to form a distally facing beveled surface and a proximally facing abutment surface. Ends of the flexible protrusions slide over the distally facing beveled surface of the locking flange during the injection cycle and engage the proximally facing abutment surface so as to retain the plunger assembly in the bottomed out position. The plunger rod further includes a tamper prevention disk located proximal to the locking flange so as to prevent tampering with the engagement between the locking flange and the flange lock and an outwardly extending flange at a proximal end thereof. The plunger rod has a variable diameter and tapers inwardly toward the flange lock.

The plunger head further includes a distal wall, the distal wall having the distal sealing surface defined thereon; a proximal wall, spaced from the distal wall; and a central portion extending between the distal wall and the proximal wall, the central portion having a cylindrical core portion and a plurality of equally spaced fin portions extending radially from the cylindrical core portion. The distal wall of the plunger head perimetrically engages the inner surface of the barrel so as to seal the chamber of the barrel.

The distal end of the plunger rod is slidably connected to the plunger head such that during the injection cycle the plunger rod slides with respect to the plunger head. The plunger head includes a cylindrical connecting portion extending from the proximal wall of the plunger head, the cylindrical connecting portion having an annular lip at a proximal end thereof. The plunger rod has a hollow cylindrical shape defining an outer surface and an inner diameter, the inner diameter of the plunger rod having an internal annular ring adapted to engage the annular lip of the cylindrical connecting portion such that the internal annular ring of the plunger rod is able to slide over the annular lip in the distal direction and retain the annular lip of the cylindrical connecting portion within the plunger rod. The plunger rod slides with respect to the cylindrical connecting portion of the plunger head such that the internal annular ring of the plunger rod engages the annular lip of the cylindrical connecting portion during aspiration and the distal end of the plunger rod engages the proximal wall of the plunger head during injection. A force necessary to advance the plunger rod relative to the plunger head during the injection cycle between aspiration and injection is less than a force necessary to sustain injection.

The plunger rod further includes an annular flange extending from the outer surface of the plunger rod at the distal end of the plunger rod, the annular flange having a diameter slightly less than or equal to a diameter of the inside surface of the syringe barrel. The plunger head may be made from a plastic material or an elastomeric material.

According to a further aspect of the present invention, a method of actuating a syringe assembly is provided. The method includes the step of providing a syringe assembly that includes a syringe barrel having an inside surface defining a chamber, an open proximal end, a distal end, and an outlet disposed adjacent the distal end in fluid communication with the chamber; a plunger assembly disposed at least partially within the syringe barrel, including an elongate plunger rod having cylindrical shape defining an outer surface, a proximal end, a distal end, and a locking flange formed thereon between the proximal and distal ends; a plunger head having a distal sealing surface; and a flange lock disposed at the open proximal end of the barrel, the flange lock including a plurality of flexible protrusions extending proximally from the open proximal end of the syringe barrel and distributed around a periphery of the open proximal end of the syringe barrel. The plunger head is inserted into the chamber of the syringe barrel to a position proximate to the distal end of the syringe barrel such that the protrusions of the flange lock fold into the chamber toward the inside surface of the syringe barrel and spring back after insertion of the plunger head is completed. The plunger rod is inserted into the chamber of the syringe barrel such that the protrusions of the flange lock fold into the chamber toward the inside surface of the syringe barrel and are held in a folded position by the outer surface of the plunger rod. The distal end of the plunger rod is connected with the plunger head such that the plunger rod is slidable with respect to the plunger head. The plunger assembly is drawn from the position proximate to the distal end of the syringe barrel in a proximal direction with the plunger head in an extended position from the distal end of the plunger rod so as to aspirate the chamber of the syringe barrel. The plunger assembly is advanced within the chamber of the syringe barrel so that the plunger rod slides with respect to the plunger head to a collapsed position with respect to the plunger head. The plunger assembly is further advanced within the chamber of the syringe barrel. The locking flange on the plunger rod is engaged with the protrusions of the flange lock so as to retain the plunger assembly in a locked position at least partially within the chamber of the syringe barrel and disable the syringe assembly.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
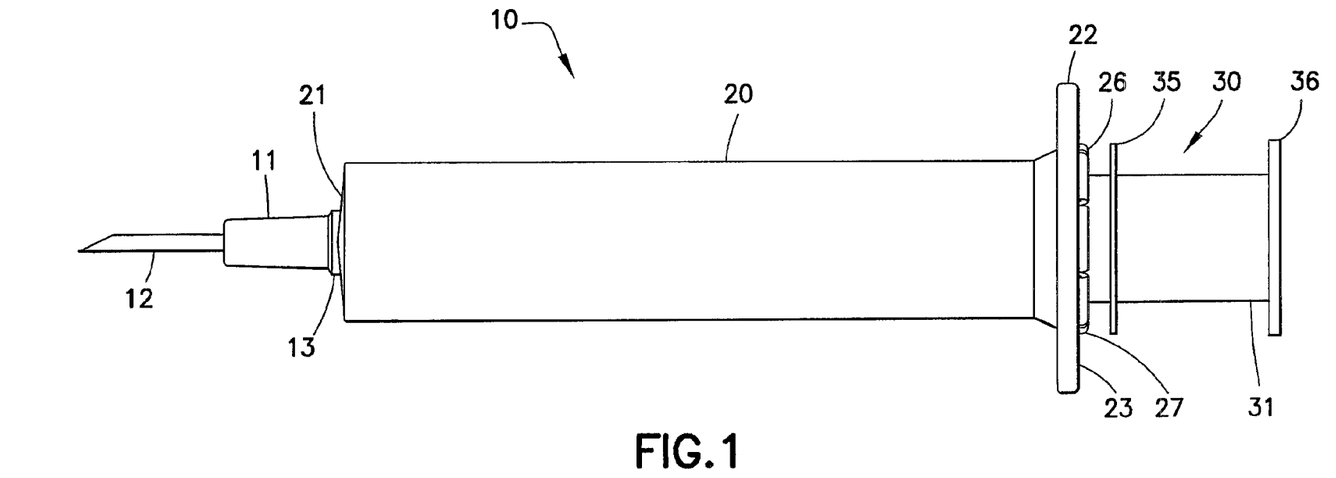
FIG. 1 is a side view of a passive reuse prevention syringe assembly in accordance with an embodiment of the present invention.

Referring to FIG. 1, a syringe assembly 10 according to an embodiment of the present invention is shown. The syringe assembly 10 includes a syringe barrel 20 and a plunger assembly 30. As shown in FIGS. 1-4, the syringe barrel 20 has an open proximal end 23 and a distal end 21 opposite to the open proximal end 23. The syringe barrel 20 has an inside surface 24, which defines a chamber 25. The syringe barrel 20 also includes an outlet 11 disposed on the distal end 21 of the syringe barrel 20. The outlet 11 is in fluid communication with the chamber 25 of the syringe barrel 20. A needle cannula 12 may be attached to the outlet 11 such that an interior of the needle cannula 12 is in fluid communication with the chamber 25 of the syringe barrel 20. As shown, the syringe barrel 20 may have a cylindrical or substantially cylindrical shape, and may include an outwardly extending flange 22 at the open proximal end 23, though it is to be appreciated that the syringe barrel 20 may be formed in any suitable shape. Additionally, the syringe barrel 20 may be injection molded from thermoplastic material such as polypropylene and polyethylene according to techniques known to those of ordinary skill in the art, though it is to be appreciated that the syringe barrel 20 may be made from other suitable materials and according to other applicable techniques.

Also as shown in FIG. 1, the needle cannula 12 may be secured within the outlet 11 by a chemical adhesive, such as epoxy, or may be mechanically affixed to the outlet 11 according to known techniques. For instance, the outlet 11 may be modified to receive a separate needle hub thereon via a standard luer taper fitting or luer lock fitting. The syringe assembly 10 may also include a protective cap (not shown) disposed over the outlet 11 to protect the needle cannula 12 prior to use and to prevent accidental needle sticks of persons handling the syringe assembly 10 prior to use. An annular ridge 13 may be formed on the distal end 21 of the syringe barrel 20 to facilitate attachment of a protective cap or a standard needle hub over the outlet 11.

Figure 2:
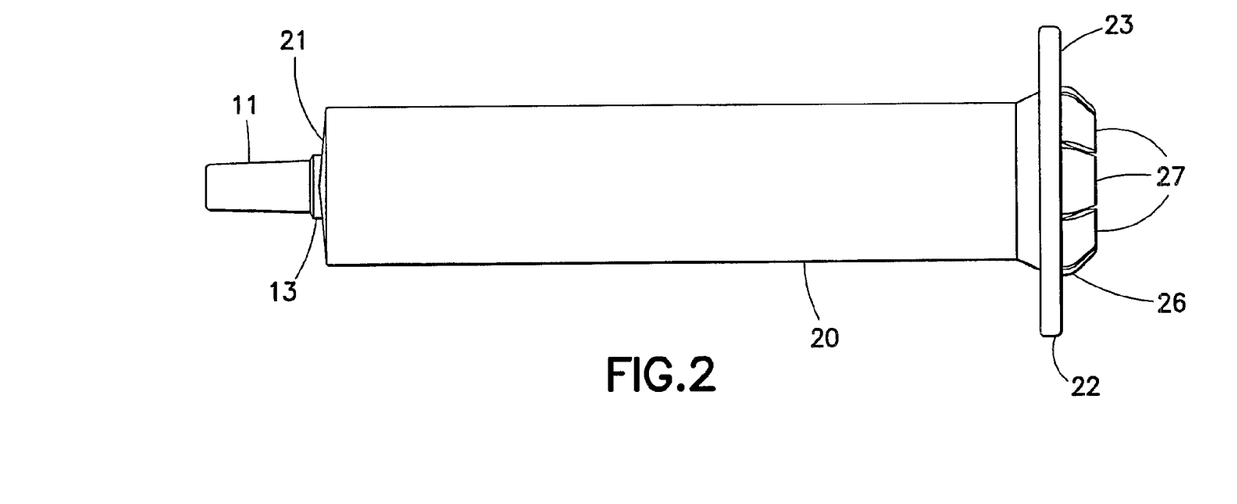
FIG. 2 is a side view of a syringe barrel and flange lock of the syringe assembly shown in FIG. 1.
Figure 3:
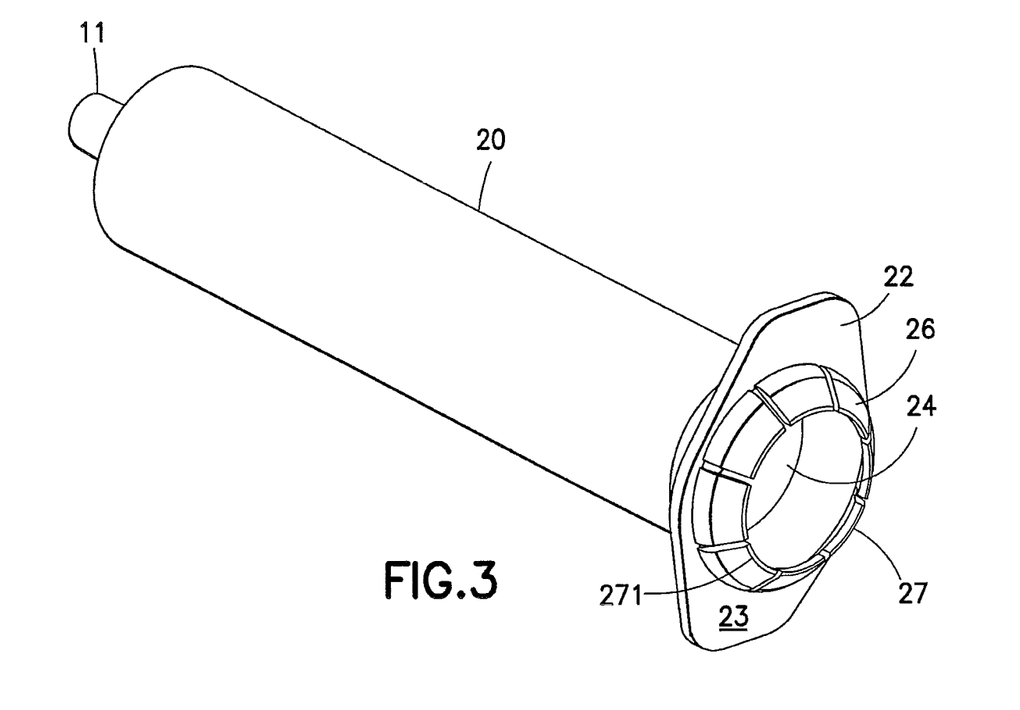
FIG. 3 is a rear perspective view of the syringe barrel and flange lock of FIG. 2.
Figure 4:
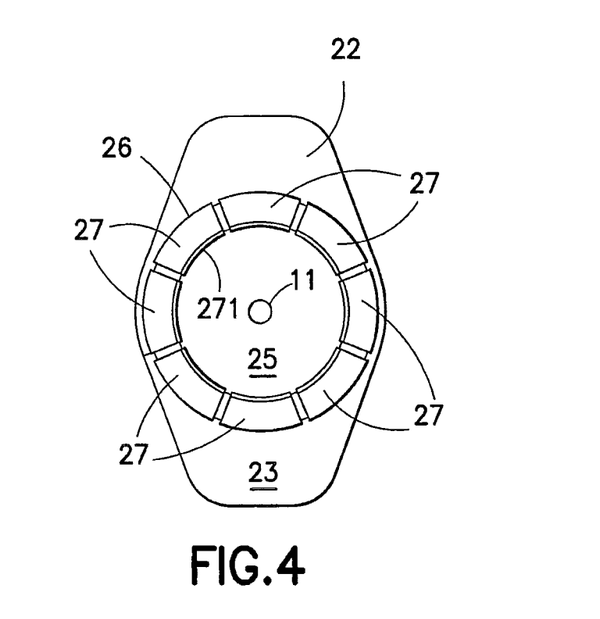
FIG. 4 is a rear view of the syringe barrel and flange lock of FIG. 2.
Figures 15, 16:
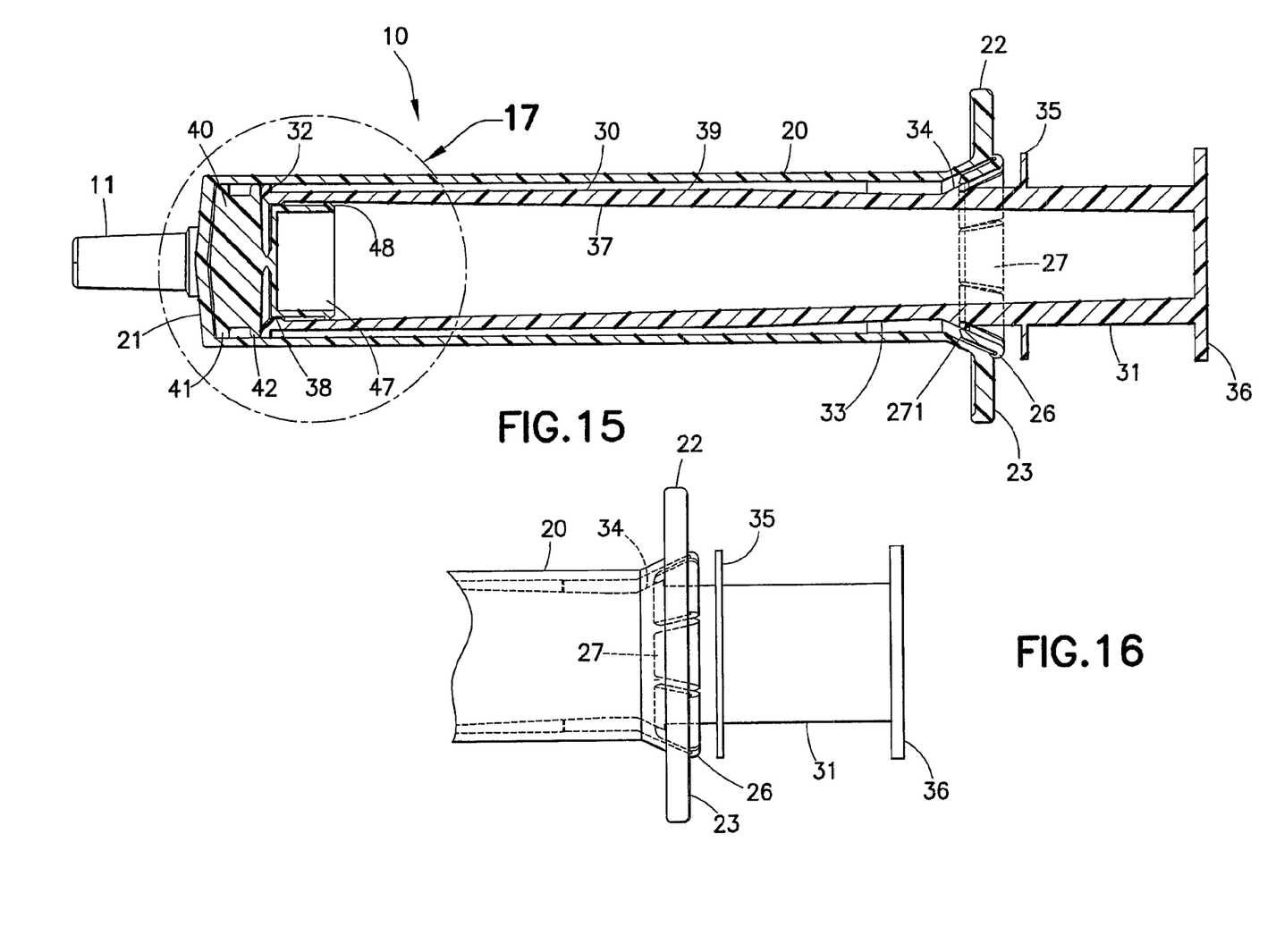
FIG. 15 is an enlarged partial cross-sectional side view of the syringe assembly after completion of an injection cycle showing the plunger assembly in a locked position.
FIG. 16 is an enlarged partial side view of the syringe assembly of FIG. 15 further illustrating an engagement between the flange lock and the plunger rod.

With further reference to FIGS. 1-4, a flange lock 26 is disposed at the open proximal end 23 of the barrel 20. The flange lock 26 includes a plurality of flexible protrusions 27 distributed around a periphery of the open proximal end 23 of the syringe barrel 20 and extend from the open proximal end 23 of the syringe barrel 20 to free ends 271. As shown, the protrusions 27 are integral with the open proximal end 23 of the syringe barrel 20, though it is to be appreciated that the flange lock 26 and protrusions 27 may be formed separately and attached to the syringe barrel 20 by techniques known to those of ordinary skill in the art. As shown in FIGS. 2-4, in an initial condition, the protrusions 27 extend proximally from the open proximal end 23 of the syringe barrel 20. As shown in FIGS. 1 and 16, the protrusions are adapted to be folded to extend distally into the chamber 25 and flex toward the inside surface 24 of the syringe barrel 20. Alternatively, the flange lock 26 may be formed such that the protrusions 27 extend distally into the chamber 25 or parallel to the open proximal end 23 of the barrel 20 in an initial condition.

Figure 5:
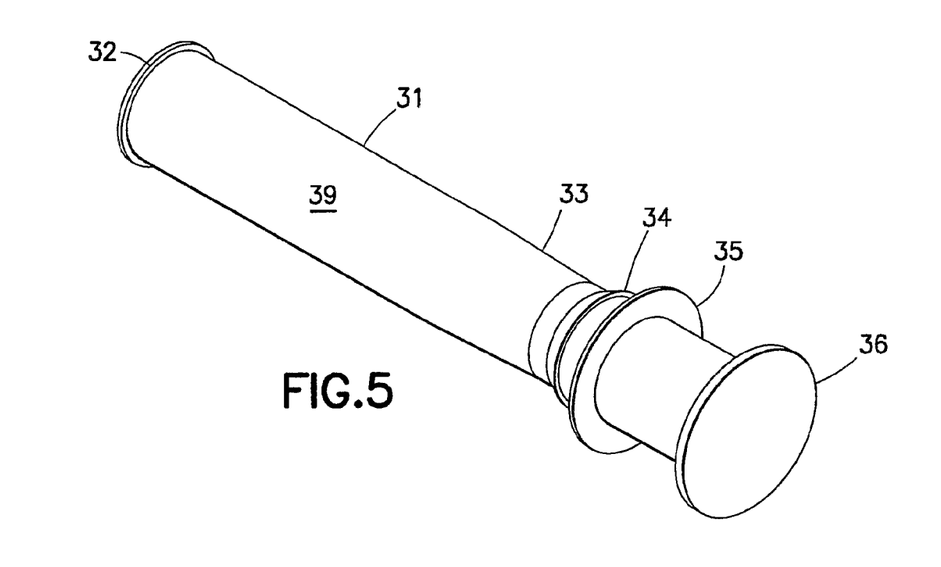
FIG. 5 is a rear perspective view of a plunger rod of the syringe assembly shown in FIG. 1.
Figure 6:
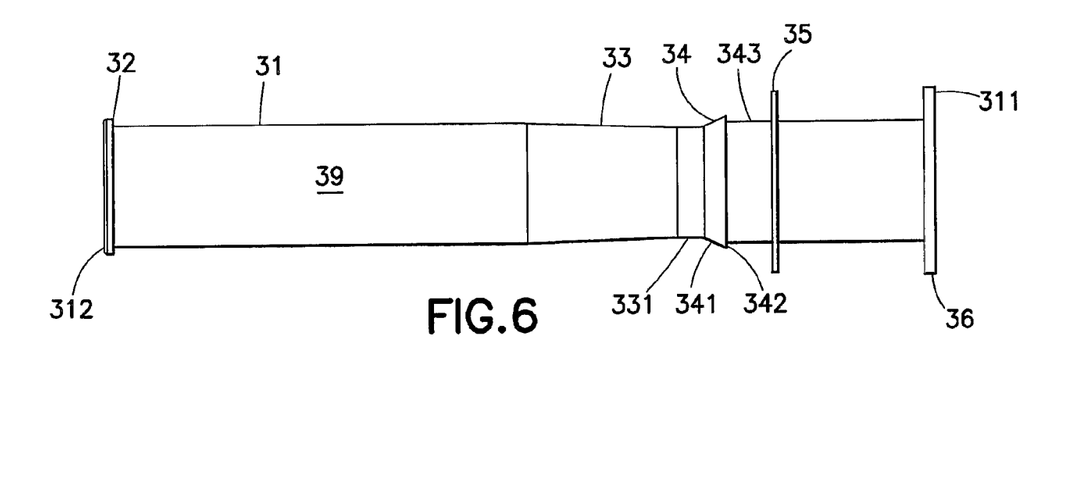
FIG. 6 is a side view of the plunger rod of FIG. 5.

With reference to FIGS. 1, 5, and 6, the plunger assembly 30 is disposed at least partially within the syringe barrel 20. The plunger assembly 30 includes an elongate plunger rod 31 having a cylindrical shape defining an outer surface 39. The plunger rod 31 has a proximal end 311 defined by an outwardly extending flange 36 and a distal end 312 defined by an annular flange 32. A locking flange 34 is formed on the plunger rod 31 between the proximal 311 and distal 312 ends. Specifically, the locking flange 34 is located on the plunger rod 31 approximately two-thirds of the length of the plunger rod 31 from the distal end 312 of the plunger rod 31 such that the plunger rod 31 may be inserted nearly the full length of the chamber 25 of the syringe barrel 20 without engaging the flange lock 26.

As shown in FIGS. 5 and 6, the locking flange 34 tapers outwardly from the outer surface 39 of the plunger rod 31 so as to form a distally facing beveled surface 341 and a proximally facing abutment surface 342. A large diameter portion 343 of the plunger rod 31 is located directly proximal of the proximally facing abutment surface 342 of the locking flange 34. The plunger rod 31 also includes tamper prevention disk 35 located proximal to the locking flange 34. The plunger rod 31 has a variable diameter. Specifically, the plunger rod 31 includes a portion 33 that tapers inwardly toward the locking flange 34. The plunger rod 31 also includes a uniform diameter portion 331 located between the inwardly tapering portion 33 and the distally facing beveled surface 341 of the locking flange 34. The plunger rod 31 may be inserted into the chamber 25 of the syringe barrel 20 in a packaged state. Preferably, in the packaged condition, the plunger rod 31 will be inserted into the syringe barrel 20 such that the protrusions 27 expand to conform to the inwardly tapering portion 33 and/or the uniform diameter portion 331 of the plunger rod 31, i.e., the portion of the plunger rod 31 having the smallest diameter. This reduces deformation of the protrusions 27 prior to use so as to ensure that the protrusions 27 will be sufficiently elastic to engage the large diameter portion 343 and the proximally facing abutment surface 342 of the locking flange 34 to prevent removal of the plunger rod 31 from the syringe barrel 20.

Figure 14:
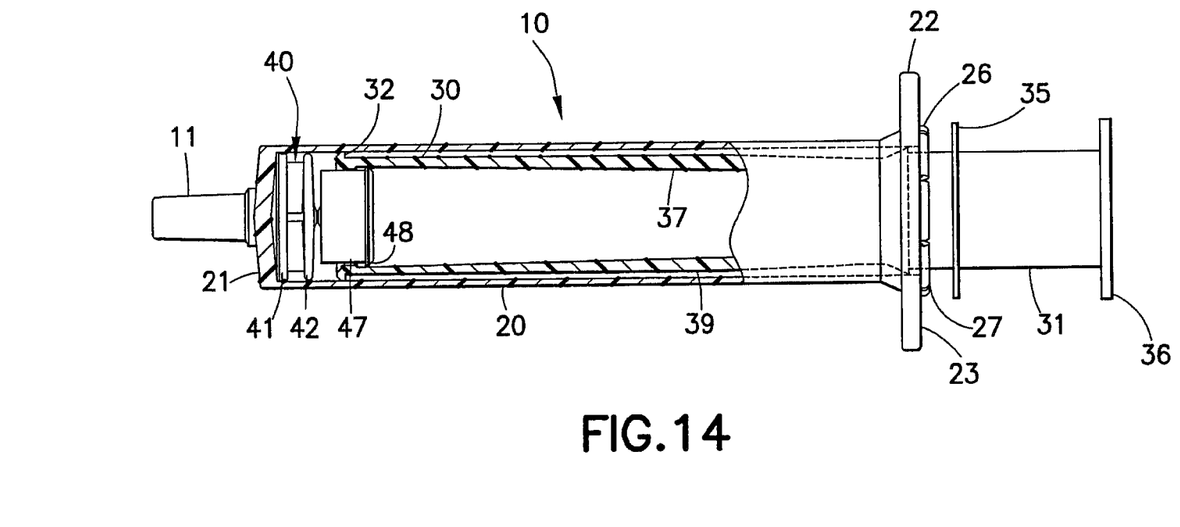
FIG. 14 is a partial cross-sectional side view of the syringe assembly prior to aspiration of the syringe barrel as the plunger rod engages the plunger head.
Figure 17:
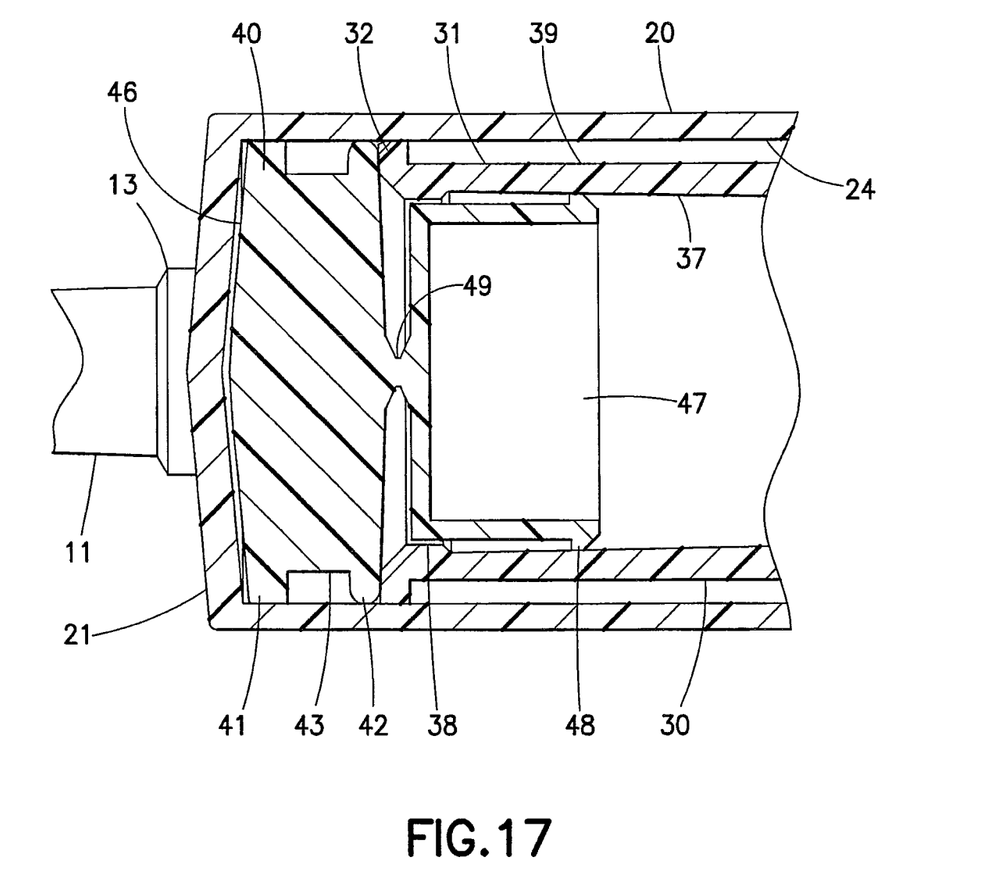
FIG. 17 is an enlarged partial cross-sectional side view of the syringe assembly of FIG. 15 further illustrating an engagement between the plunger rod and the plunger head.

As shown in FIGS. 14-16, the tamper prevention disk 35 is sized and spaced from the locking flange 34 such that the tamper prevention disk 35 prevents healthcare workers and others from tampering with an engagement between the flange lock 26 on the syringe barrel 20 and the locking flange 34. Also, as shown in FIGS. 15 and 17, the plunger rod 31 is hollow and has an inner diameter 37. The inner diameter 37 of the plunger rod 31 includes an internal annular ring 38 adjacent to the distal end 312 of the plunger rod 31. Further, the annular flange 32 at the distal end 312 of the plunger rod 31 has a diameter slightly less than or equal to the diameter of the inside surface 24 of the syringe barrel 20, such that the flange 32 is able to engage against the free ends 271 of the protrusions 27 of the flange lock 26 to prevent removal of the plunger rod 31 from the syringe barrel 20. The annular flange 32 also stabilizes the position of the plunger rod 31 within the syringe barrel 20 and facilitates alignment of the distal end 312 of the plunger rod 31 within the chamber 25 and the connection to plunger head 40, as will be discussed below.

Figure 7:
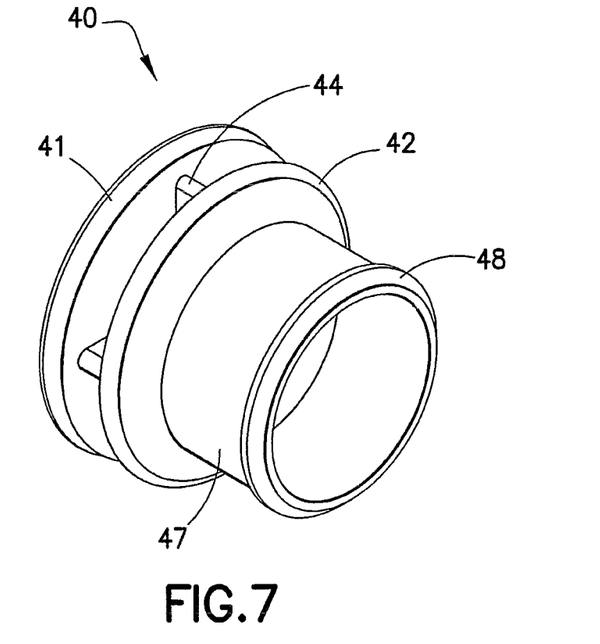
FIG. 7 is a rear perspective view of a plunger head of the syringe assembly shown in FIG. 1.
Figure 8:
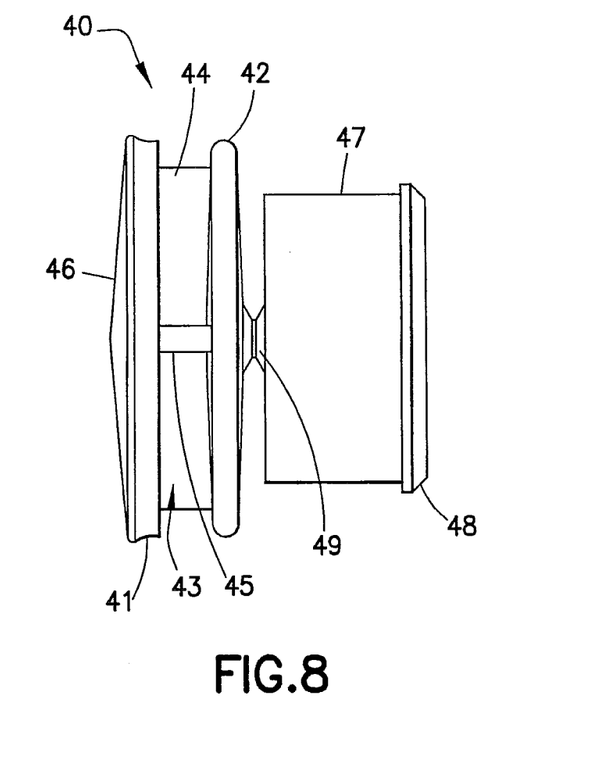
FIG. 8 is a side view of the plunger head of FIG. 7.

With reference to FIGS. 7 and 8, the plunger assembly 30 also includes a plunger head 40. The plunger head 40 includes a distal wall 41 and a proximal wall 42. The distal wall 41 has a distal sealing surface 46 of the plunger head 40 defined thereon. As shown in FIGS. 15 and 17, the distal wall 41 of the plunger head 40 perimetrically engages the inside surface 24 of the syringe barrel 20 so as to seal the chamber 25 of the syringe barrel 20 during use of the syringe assembly 10. The distal and proximal walls 41, 42 of the plunger head 40 are spaced by a central portion 43 of the plunger head 40 that extends between the distal and proximal walls 41, 42 of the plunger head 40. The central portion 43 has a cylindrical core portion 45 and a plurality of fin portions 44 extending radially from the cylindrical core portion 45, which may be equally spaced about the cylindrical core portion 45. As shown, there are four fin portions 44, though there could be more or less so long as the distal wall 41 of the plunger head 40 is suitably supported against canting, thus breaking a sealing engagement between the distal wall 41 and the inside surface 24 of the syringe barrel 20 during use.

As shown in FIGS. 7 and 8, the plunger head 40 further includes a cylindrical connecting portion 47 extending from the proximal wall 42 of the plunger head 40. The cylindrical connecting portion 47 includes an annular lip 48 at a proximal end thereof. As shown, the cylindrical connecting portion 47 is integrally connected to the proximal wall 42 of the plunger head 40 by a neck portion 49. It is to be appreciated that the cylindrical connecting portion 47 may be formed separately from the plunger head 40 and attached to the proximal wall 42 of the plunger head 40 by an adhesive or may be mechanically affixed to the proximal wall 42 according to known techniques.

The plunger head 40 may be integrally molded from either a soft plastic material, such as polyurethane, or alternatively may be formed from a rubber or elastomeric material depending upon choice. Such versatility and interchangeability within the syringe assembly 10 is advantageous because all plastic components can be used in markets where cost is extremely important and an elastomeric plunger head 40 can be used in markets with a strong preference for such components. It is to be appreciated that the plunger head can be formed in different shapes and according to other techniques known to be suitable to those of ordinary skill in the art.

As shown in FIGS. 13-15 and 17, the distal end 312 of the plunger rod 31 is engageable with the cylindrical connecting portion 47 of the plunger head 40 so that the plunger rod 31 is able to move the plunger head 40 within the chamber 25 of the syringe barrel 20 through an injection cycle. Particularly, the distal end 312 of the plunger rod 31 is slidably connected to the plunger head 40 such that during the injection cycle the plunger rod 31 slides with respect to the plunger head 40. The cylindrical connecting portion 47 fits within the inner diameter 37 of the hollow plunger rod 31 such that the internal annular ring 38 of the plunger rod 31 is able to engage the annular lip 48 of the cylindrical connecting portion 47 by sliding over the annular lip 48 in the distal direction and thereafter retain the annular lip 48 of the cylindrical connecting portion 47 with the plunger rod 31 so as to slidably connect the distal end 312 of the plunger rod 31 with the plunger head 40. During an injection cycle, the distal end 312 of the plunger rod 31 slides with respect to the cylindrical connecting portion 47 of the plunger head 40 such that the internal annular ring 38 of the plunger rod 31 engages the annular lip 48 of the cylindrical connecting portion 47 during aspiration of the syringe barrel 20 and the distal end 312 of the plunger rod 31 passes over the cylindrical connecting portion 47 and abuttingly engages the proximal wall 42 of the plunger head 40 during injection of the contents of the syringe barrel 20.

Figure 9:
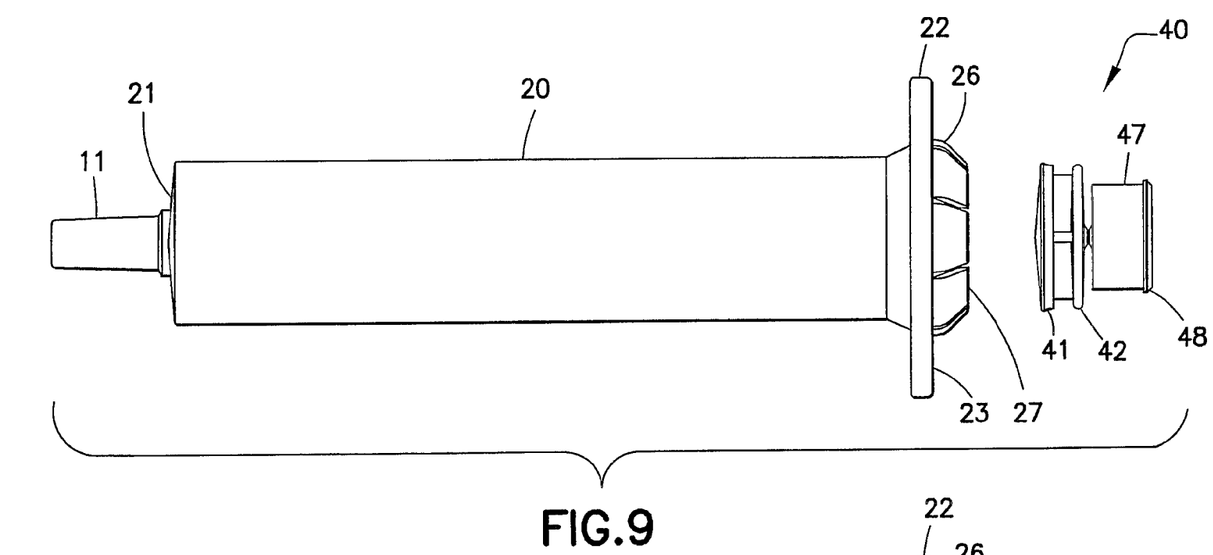
FIG. 9 is a side view of the syringe barrel and flange lock and the plunger head of the syringe assembly prior to insertion of the plunger head into the chamber of the syringe barrel.
Figure 10:
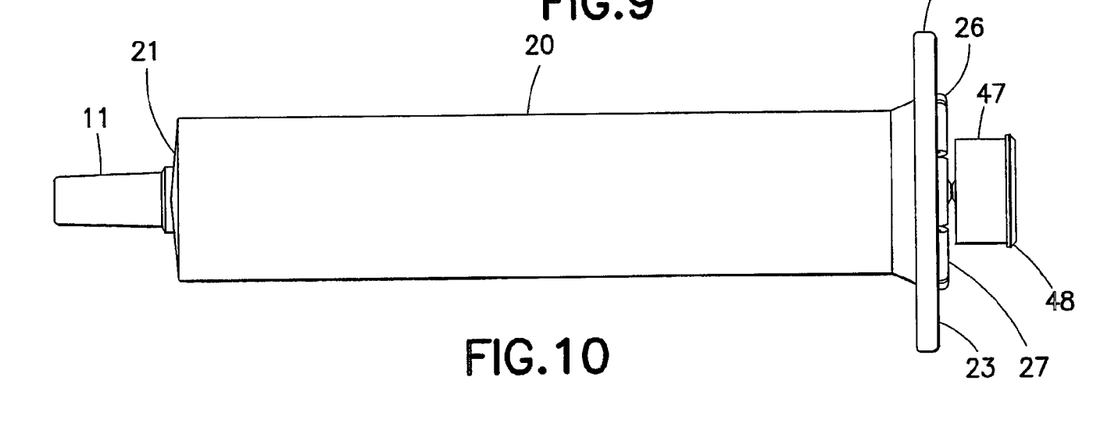
FIG. 10 is a side view of the syringe barrel and flange lock and the plunger head of the syringe assembly as the plunger head is inserted into the chamber of the syringe barrel.
Figure 11:
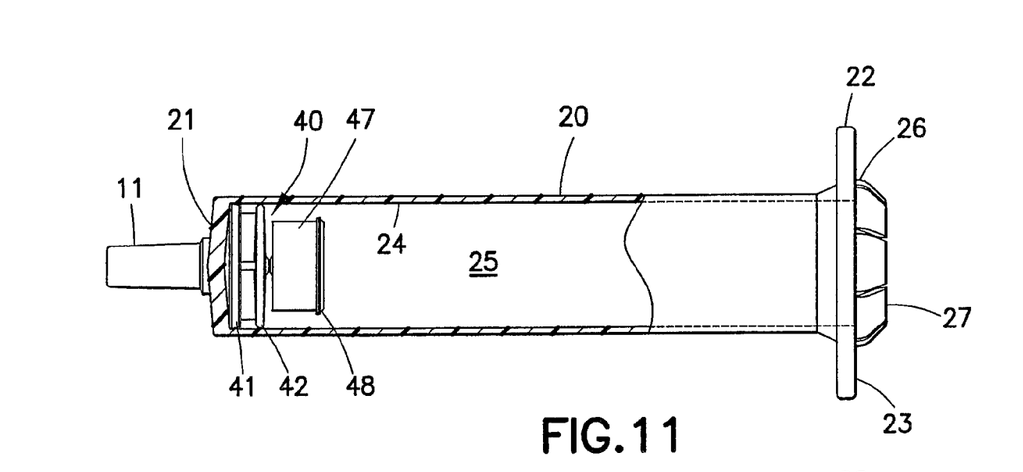
FIG. 11 is a partial cross-sectional side view of the syringe barrel and flange lock and the plunger head of the syringe assembly showing the plunger head in a bottomed out position within the chamber of the syringe barrel.

Referring to FIGS. 9-17, operation of the syringe assembly 10 according to an embodiment of the present invention will now be described in detail. As shown in FIGS. 9-11, at an initial state of the syringe assembly 10, the plunger head 40 is inserted into the chamber 25 of the syringe barrel 20 via the open proximal end 23 to a position proximate to the distal end 21 of the syringe barrel 20, particularly a bottomed out position within the chamber 25. As the plunger head 40 is inserted into the chamber 25, the protrusions 27 of the flange lock 26 will fold into the chamber 25 toward the inside surface 24 of the syringe barrel 20. Once the plunger head 40 passes through the flange lock 26, the protrusions 27 may spring back into their initial condition. It is to be appreciated that the syringe assembly 10 may be packaged with the plunger head 40 already fully inserted into the chamber 25 of the syringe barrel 20 and with the plunger rod 31 inserted into the chamber 25 of the syringe barrel 20 and attached to the plunger head 40, as shown in FIG. 14. Alternatively, the plunger head 40 and the plunger rod 31 may be packaged separately from the syringe barrel 20 and then manually inserted by a healthcare worker or technician prior to use.

Figure 12:
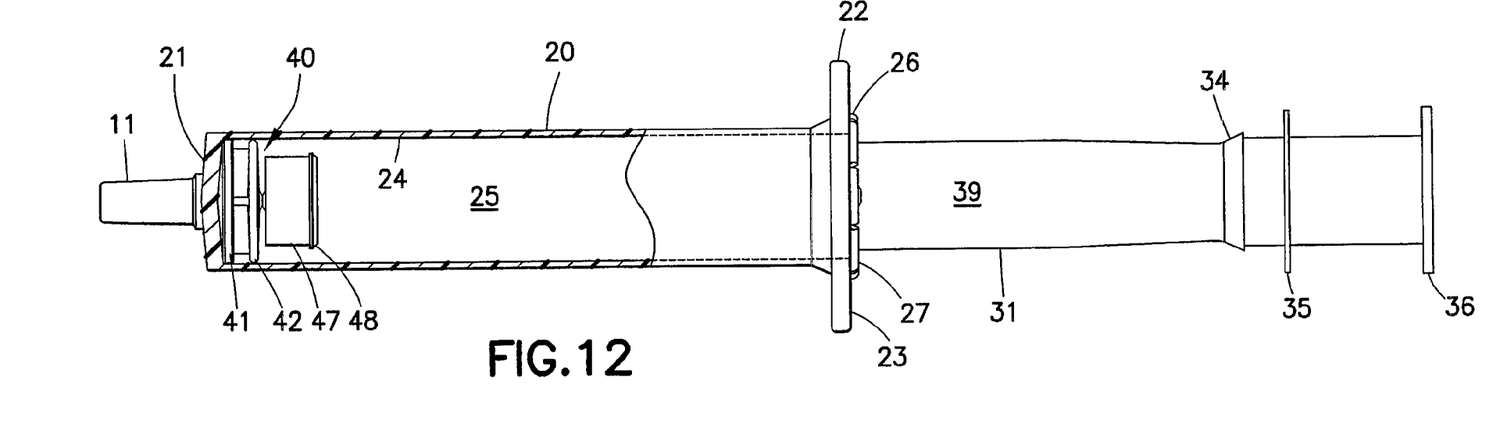
FIG. 12 is a partial cross-sectional side view of the syringe assembly as the plunger rod is inserted into the chamber of the syringe barrel.
Figure 13:
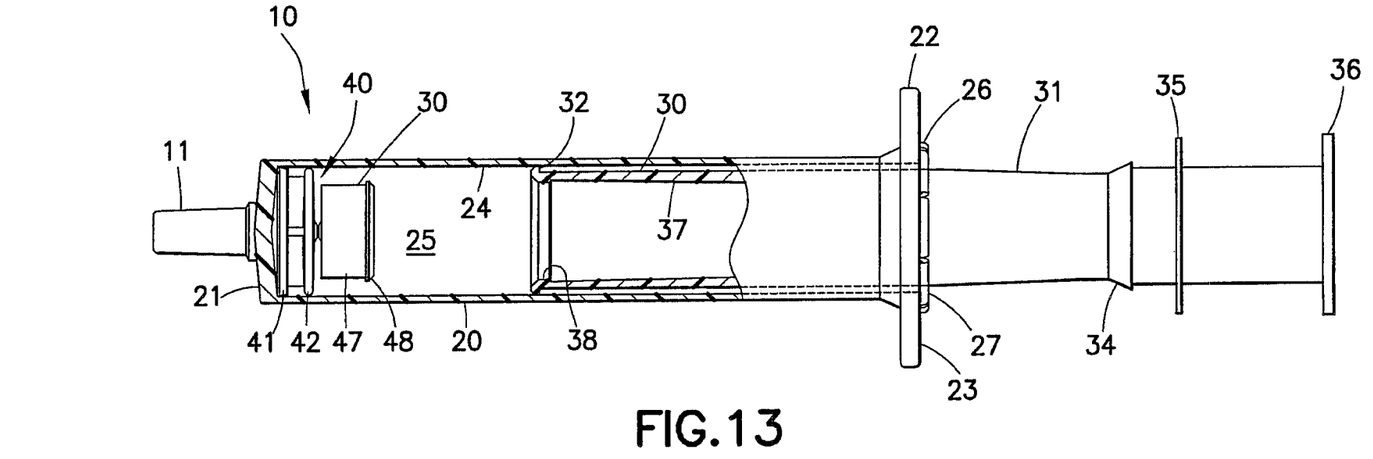
FIG. 13 is a partial cross-sectional side view of the syringe assembly as the plunger rod is inserted further into the chamber of the syringe barrel.

As shown in FIGS. 12-14, the plunger rod 31 is then inserted into the chamber 25 via the open proximal end 23 of the syringe barrel 20 so as to be disposed at least partially within the chamber 25. As the plunger rod 31 is inserted into the chamber 25, the protrusions 27 of the flange lock 26 fold into the chamber 25 toward the inside surface 24 of the syringe barrel 20 and are held in a folded position by the outer surface 39 of the plunger rod 31. As the plunger rod 31 is further inserted into the chamber 25, the distal end 312 of the plunger rod 31 will come into engagement with the cylindrical connecting portion 47 of the plunger head 40, as discussed above, so as to connect the distal end 312 of the plunger rod 31 with the plunger head 40 such that the plunger rod 31 is slidable with respect to the cylindrical connecting portion 47 of the plunger head 40.

During aspiration, the plunger rod 31 is drawn from the syringe barrel 20 in the proximal direction. As this occurs, the plunger rod 31 may initially slide with respect to the cylindrical connecting portion 47 of the plunger head 40 until the internal annular ring 38 of the plunger rod 31 engages the annular lip 48 of the cylindrical connecting portion 47 and the plunger head 40 is drawn proximally by the plunger rod 31 in an extended position so as to aspirate the chamber 25 of the syringe barrel 20.

Once the desired aspiration of the chamber 25 of the syringe barrel 20 is completed, the plunger rod 31 is advanced within the chamber 25 of the syringe barrel 20. As the plunger rod 31 is advanced, the distal end 312 of the plunger rod 31 slides with respect to cylindrical connecting portion 47 of the plunger head 40 until the distal end 312 of the plunger rod 31 engages the proximal wall 42 of the plunger head 40 in a collapsed position. The plunger assembly 30 is then further advanced within the chamber 25 of the syringe barrel 20 with the plunger head 40 being pushed through the chamber 24 by the distal end 312 of the plunger rod 31 so as to inject the contents of the chamber 25 into a patient. Thus, it is to be appreciated that a force necessary to advance the plunger rod 31 relative to the plunger head 40 during the injection cycle between aspiration and injection is less than a force necessary to sustain injection of the contents of the chamber 25 of the syringe barrel 20. By providing a collapsible plunger assembly 30 with a slidable connection between the plunger rod 31 and the plunger head 40, the plunger head 40 can be initially packaged in a bottomed out condition, i.e., abutting or adjacent to the distal end 21 of the syringe barrel 20. This results in less air being drawn into the chamber 25 of the syringe barrel 20 during aspiration and prior to injection. It is to be appreciated that the plunger assembly 30 could alternatively be formed with the plunger head 40 integral with the plunger rod 31 or otherwise non-slidably connected to the plunger rod 31 according to known techniques.

As shown in FIGS. 15 and 16, during the injection cycle, the protrusions 27 of the flange lock 26 slide along the outer surface 39 of the plunger rod 31 and engage the locking flange 34 of the plunger rod 31 upon or substantially upon completion of the injection cycle so as to retain the plunger assembly 30 in a bottomed out position with the distal sealing surface 46 of the plunger head 40 abutting, or nearly abutting, against the distal end 21 of the syringe barrel 20 to prevent removal of the plunger rod 31 from the syringe barrel 20, thereby retaining the plunger assembly 30 in a locked position at least partially within the chamber 25 of the syringe barrel 20 and disabling the syringe assembly 10. More particularly, as the plunger head 40 reaches the bottomed out position and the contents of the chamber 25 of the syringe barrel 20 are fully injected to complete the injection cycle, the ends 271 of the flexible protrusions 27 slide over the distally facing beveled surface 341 of the locking flange 34 and engage the proximally facing abutment surface 342 so as to retain the plunger assembly 30 in the bottomed out position. Alternatively, the locking flange 34 may be positioned on the plunger rod 31 such that the locking flange 34 moves distally beyond the flange lock 26 during the injection cycle prior to full injection of the contents of the syringe barrel 20 so as to prevent removal of the plunger rod 31 from the syringe barrel 20.

While several embodiments of a passive reuse prevention syringe that uses a flange lock and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A syringe assembly, comprising:
a syringe barrel having an inside surface defining a chamber, an open proximal end, a distal end, and an outlet disposed adjacent the distal end in fluid communication with the chamber;
a plunger assembly disposed at least partially within the syringe barrel, comprising an elongate plunger rod having a proximal end, a distal end, a locking flange formed thereon between the proximal and distal ends, and a plunger head, the plunger rod being engageable with the plunger head such that the plunger rod is adapted to move the plunger head within the chamber of the syringe barrel through an injection cycle; and
a flange lock disposed at the open proximal end of the barrel,
wherein the plunger rod has a cylindrical shape defining a cylindrical outer surface extending from the distal end of the plunger rod to the proximal end of the plunger rod and the locking flange is formed on the outer surface of the plunger rod,
wherein the flange lock is integral with the open proximal end of the syringe barrel,
wherein during the injection cycle, the flange lock engages the locking flange of the plunger rod so as to retain the plunger head at or near a bottomed out position abutting the distal end of the syringe barrel and to prevent removal of the plunger rod from the syringe barrel, and
wherein the flange lock is configured to slidingly engage the cylindrical outer surface of the plunger rod during the injection cycle prior to engaging the locking flange of the plunger rod.

2. The syringe assembly according to claim 1, wherein the flange lock includes a plurality of flexible protrusions distributed around a periphery of the open proximal end of the syringe barrel.

3. The syringe assembly according to claim 2, wherein the protrusions extend proximally from the open proximal end of the syringe barrel.

4. The syringe assembly according to claim 2, wherein the protrusions extend distally from the open proximal end of the syringe barrel into the chamber of the barrel.

5. The syringe assembly according to claim 2, wherein
the flexible protrusions of the flange lock are adapted to flex toward the inside surface of the barrel as the plunger rod is inserted into the chamber of the barrel, and
during the injection cycle, the protrusions slide along the outer surface of the plunger rod and engage the locking flange on the plunger rod so as to retain the plunger assembly in the barrel of the syringe and disable the syringe assembly.

6. The syringe assembly according to claim 5, wherein
the locking flange on the plunger rod tapers outwardly from the outer surface of the plunger rod so as to form a distally facing beveled surface and a proximally facing abutment surface, and
ends of the flexible protrusions slide over the distally facing beveled surface of the locking flange during the injection cycle and engage the proximally facing abutment surface so as to retain the plunger assembly in the barrel of the syringe.

7. The syringe assembly according to claim 1, wherein the plunger rod further includes a tamper prevention disk located proximal to the locking flange so as to prevent tampering with the engagement between the locking flange and the flange lock.

8. The syringe assembly according to claim 1, wherein the plunger rod has a variable diameter.

9. The syringe assembly according to claim 8, wherein the plunger rod tapers inwardly toward the flange lock.

10. The syringe assembly according to claim 1, wherein the plunger head further comprises:
a distal wall, the distal wall having a distal sealing surface defined thereon;
a proximal wall, spaced from the distal wall; and
a central portion extending between the distal wall and the proximal wall, the central portion having a cylindrical core portion and a plurality of fin portions extending radially from the cylindrical core portion, and
wherein the distal wall of the plunger head perimetrically engages the inner surface of the barrel so as to seal the chamber of the barrel.

11. The syringe assembly according to claim 1, wherein the distal end of the plunger rod is slidably connected to the plunger head.

12. The syringe assembly according to claim 11, wherein
the plunger head includes a cylindrical connecting portion extending from a proximal wall of the plunger head, the cylindrical connecting portion having an annular lip at a proximal end thereof,
the plunger rod has a hollow cylindrical shape defining an outer surface and an inner diameter, the inner diameter of the plunger rod having an internal annular ring adapted to engage the annular lip of the cylindrical connecting portion such that the internal annular ring of the plunger rod is able to slide over the annular lip in the distal direction and retain the annular lip of the cylindrical connecting portion within the plunger rod, and
the plunger rod slides with respect to the cylindrical connecting portion of the plunger head such that the internal annular ring of the plunger rod engages the annular lip of the cylindrical connecting portion during aspiration and the distal end of the plunger rod engages the proximal wall of the plunger head during injection.

13. The syringe assembly according to claim 12, wherein a force necessary to advance the plunger rod relative to the plunger head during the injection cycle between aspiration and injection is less than a force necessary to sustain injection.

14. The syringe assembly according to claim 12, wherein the plunger rod further includes an annular flange extending from the outer surface of the plunger rod at the distal end of the plunger rod, the annular flange having a diameter slightly less than or equal to a diameter of the inside surface of the syringe barrel.

15. A plunger assembly for a syringe, the plunger assembly comprising:
- an elongate plunger rod having a proximal end, a distal end, and a locking flange formed thereon between the proximal and distal ends; and
- a plunger head, the plunger head including a cylindrical connecting portion,
- wherein the plunger rod is engageable with the plunger head such that the plunger rod is adapted to move the plunger head within a chamber of a syringe barrel through an injection cycle,
- wherein the distal end of the plunger rod is connected to the plunger head such that the distal end of the plunger rod slides with respect to the plunger head during the injection cycle,
- wherein during the injection cycle, the locking flange of the plunger rod is configured to engage a flange lock on the syringe so as to prevent removal of the plunger rod from the syringe barrel, and
- wherein the plunger rod has a hollow cylindrical shape defining an outer surface and an inner diameter, and the cylindrical connecting portion of the plunger head fits within the inner diameter of the plunger rod.

16. The plunger assembly according to claim 15, wherein the locking flange on the plunger rod tapers outwardly from the outer surface of the plunger rod so as to form a distally facing beveled surface and a proximally facing abutment surface.

17. The plunger assembly according to claim 15, wherein the plunger rod further includes a tamper prevention disk located proximal to the locking flange so as to prevent tampering with the engagement between the locking flange and the flange lock.

* * * * *